United States Patent [19]

Farrington et al.

[11] Patent Number: 4,892,470
[45] Date of Patent: Jan. 9, 1990

[54] APPARATUS FOR LAYERED FLANGED FIBROUS PAD FORMATION

[75] Inventors: Allan P. Farrington, Englishtown; Gerald M. Marshall, Somerville, both of N.J.

[73] Assignee: Johnson & Johnson, New Brunswick, N.J.

[21] Appl. No.: 311,544

[22] Filed: Feb. 16, 1989

[51] Int. Cl.$^4$ .............................................. B29J 5/00
[52] U.S. Cl. .................... 425/80.1; 156/622; 156/624; 156/285; 156/500; 264/517; 425/81.1; 604/365
[58] Field of Search ...................... 19/145.5, 148, 304; 156/62.2, 62.4, 285, 328, 500; 264/112, 517, 546, 571; 425/80.1, 81.1, 82.1, 84, 85; 604/365, 380

[56] References Cited

U.S. PATENT DOCUMENTS

| | | | |
|---|---|---|---|
| 2,073,329 | 3/1937 | Winter | 264/112 |
| 2,949,646 | 8/1960 | Clark | 425/80.1 |
| 3,518,726 | 7/1970 | Banks | 28/121 |
| 3,740,797 | 6/1973 | Farrington | 425/81.1 |
| 3,846,871 | 11/1974 | Kolbach | 19/148 |
| 3,860,002 | 1/1975 | Kolbach | 604/365 |
| 3,939,240 | 2/1976 | Savich | 264/109 |
| 3,973,291 | 8/1976 | Kolbach | 19/148 |
| 4,005,957 | 2/1977 | Savich | 425/80.1 |
| 4,016,628 | 4/1977 | Kolbach | 425/82.1 |
| 4,592,708 | 6/1986 | Feist et al. | 425/80.1 |

Primary Examiner—Jay H. Woo
Assistant Examiner—Timothy W. Heitbrink
Attorney, Agent, or Firm—Joseph F. Shirtz

[57] ABSTRACT

An apparatus permitting formation of a flanged product with the wider flanged portion in engagement with a foraminous transporting device. The apparatus uses a mold-like former having a narrower or smaller portion separated from the foraminous surface by a wider flange forming portion. The flange forming portion is adjacent to the foraminous surface and is separated from the foraminous surface after pad formation leaving the formed pad behind.

10 Claims, 2 Drawing Sheets

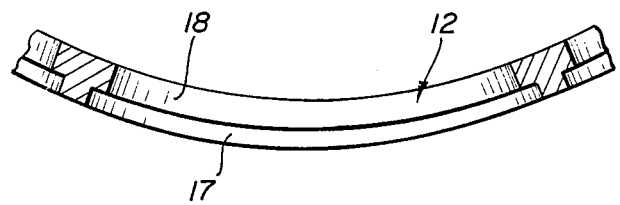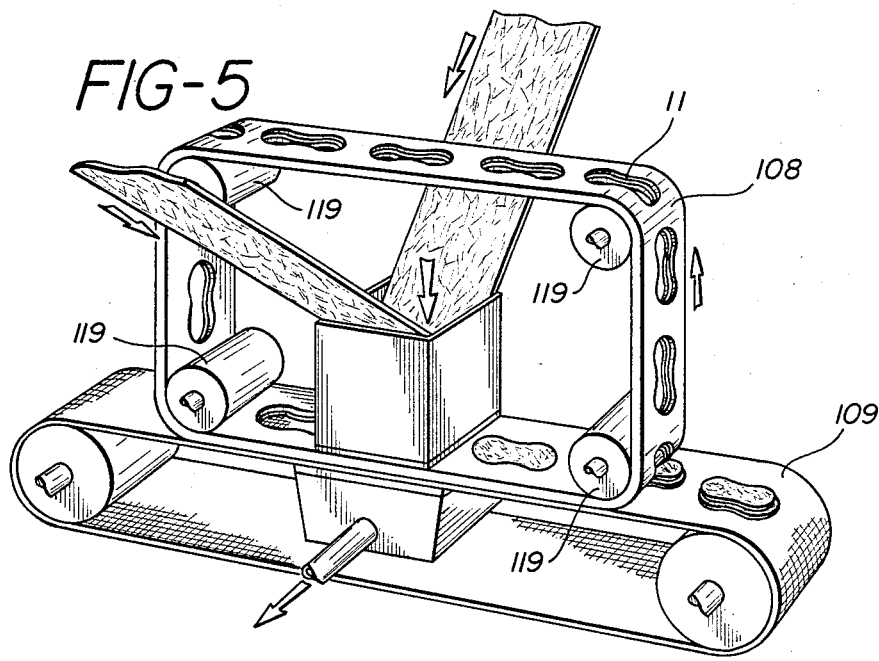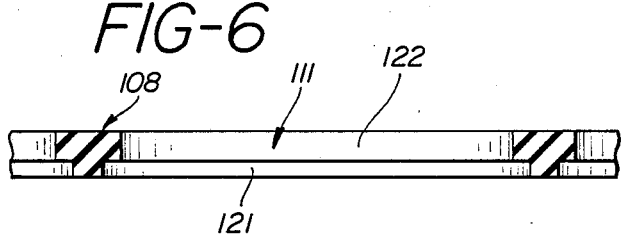

APPARATUS FOR LAYERED FLANGED FIBROUS PAD FORMATION

TECHNICAL FIELD

This invention relates to an improved method and apparatus for molding composite nonwoven web products of various shapes and sizes having flanged layers and made up of randomly oriented fibers and/or particulate matter obtained from separate supplies of individualized source material such as textile fibers, paper-making fibers and powders.

BACKGROUND

Nonwoven fiber webs frequently consist of a random yet homogeneous agglomeration of long and short fibers, Long fibers are fibers of both natural and synthetic origin that are suitable for textiles. They are longer than 0.25 inches and generally range between 0.5 and 2.5 inches in length. Short fibers are suitable for paper-making and are generally less than about 0.25 inches long, such as wood pulp fibers or cotton linters. It is known in the art that strong nonwoven webs can be made by rapidly and reliably blending inexpensive short fibers with strong long fibers.

Nonwoven fabrics are less costly than woven or knitted material, yet are more or less comparable in physical properties, appearance, and weight. Thus, inexpensive nonwoven fabrics are available for a wide variety of products, including, hand towels, table napkins, sanitary napkins, hospital clothing, draperies, cosmetic pads, etc. These nonwoven webs can be particularly advantageous when formed as a layered or composite material having a varying area in horizontal cross-section at various vertical locations.

Methods and machines for making nonwoven fluff pulp pads and pre-shaped absorbent products are known, but do not provide for selective blending and layering of pulp, textile, and particulate materials. Conventional pocket-forming devices can process only one material, usually pulp, and cannot be readily modified to provide uniformly blended pads because of the complex geometry inherent in the use of hammer mills or disc mills and cylindrical product-forming surfaces. Typical of these conventional devices are machines available from Winkler & Dunnebier Maschenfabrik and Curt G. Joa, Inc. See, for example, U.S. Pat. Nos. 4,560,379 and 4,598,441 of Stemmler. [owned by W&D]. PCT Application No. WO 85/04366 of Johnson et al. is also of interest. Johnson teaches the use of fiber-receiving molds disposed on a continuously rotating drum selectively provided with a vacuum. Other foraminous drum arrangements having circumferential cavities are taught by U.S. Pat. No. 4,592,708 of Feist et al. and U.S. Pat. No. 3,518,726 of Banks.

An early method of making sanitary napkins is disclosed in U.S. Pat. No. 2,073,329 of Winter. Winter teaches that patches of loose cotton fibers may be blown down onto a gauze-like material at regular intervals in cooperation with a suction means. Then pads of absorbent material may be placed over the cotton patches, and the gauze folded and cut at regular intervals to make the napkins. The loose cotton fibers are directed to the surface of a moving wheel having spaced and screened suction inlets adapted to receive and condense the cotton fibers in uniform patches. The Winter process requires several time-consuming and independent steps, followed by the assembly of the composite structure from its component structures. It does not provide for a composite shaped and layered structure formed by blending one or more fibrous and/or particulate materials in an integral operation.

U.S. Pat. No. 2,949,646 of Clark is also representative of the prior art, and sets forth the problem of providing three-dimensionally shaped structures having sharply defined edges. Clark recites a prior art method wherein fibers are deposited continuously from an entraining air stream onto a continuously moving foraminous belt provided with suction. The belt is partially masked in order to provide deposition and condensation of fibers into a web having the desired shape. Clark notes that this method is disfavored because of the leakage of fibers from the masked to the unmasked regions of the belt, resulting in non-uniform layers. The prior use of pans to catch fibers deposited by gravity is mentioned by Clark, as is a method of cutting web to desired shapes, or separating webs using caul plates.

The improvement of the Clark invention over the prior art is a fiber depositing head whereby unblended web structures having contoured edges are made by entraining previously individualized fibers in a circular path within a circular housing, delivering uniform volumes of entrained fibers to a moving collecting wall through openings in a foraminous separating wall of the housing, and forming a continuous web from the delivered fibers over collecting or masking members on the collecting wall. A clean separation of the continuous web into individual mats is achieved by a trough arrangement on the collecting wall, which trough separates adjacent collecting members and prevents leakage of fibers onto the collecting members by trapping excess fibers. A means for separating the masked collecting members from the end-product is also described.

A number of absorbent articles, and methods and machines for making them, are disclosed in the patents of Kolbach, U.S. Pat. Nos. 3,846,871; 3,860,002; 3,973,291; and 4,016,628. The '002 and '628 patents relate to adhesively bonded composite structures having a medial portion of grater basis weight than flanking end and side portions. These structures are obtained by providing discrete zones of relatively high and low suction on a foraminous forming surface.

The '871 and '291 patents describe a moving pad forming assembly having spaced, three-dimensional fiber-receiving compartments separated by air-impermeable regions. Each compartment has the shape of the desired end-product and is provided with a foraminous lower surface and movable air-impermeable side walls. Individualized fibers are provided to the compartments, which in turn communicate with a fiber-entraining suction means. Selective masking of the suction means can be used to influence the density and weight of material collected within regions of each compartment, and different air-suspended fibers are deposited to different compartment sections at different, non-overlapping, times to achieve different weight and density zones within each compartment.

U.S. Pat. Nos. 3,939,240 and 4,005,957 to Savich disclose a method and an apparatus for forming fibrous pads. Savich teaches a continuously driven condenser roll having three-dimensional foraminous cavities about its periphery. Each cavity is provided with a vacuum and is brought into communication with a pad forming region that is supplied with air-suspended fibers. The fibers are deposited within the cavity and form a layer, after which each layer is removed from its cavity as a pad by another vacuum cooperating with a proximate -downstream transfer conveyor. The opening into each cavity has a smaller surface area than the surface area within the cavity, so that the resulting pads are consolidated within the cavity, resulting in an increased basis weight, rather than an advantageously shaped and sharply defined composite web structure.

The prior art does not provide discrete composite nonwoven structures having predetermined shapes and consisting of layers and/or vertical zones comprising blends of long fibers, short fibers and/or particulate matter. A method and apparatus capable of providing these structures is unknown, and in particular the prior art methods do not teach a means of producing such structures in a single continuous operation.

SUMMARY OF THE INVENTION

The above-described apparatus are limited in their fiber lengths in molding because a scarfing roll is necessary to dress the final product. Scarfing of a surface having long fibers would destroy the surface. The invention provides a new method and apparatus for making flanged pad structures. Using known fiber separation and air entraining methods and apparatus, fiber streams are fed to a mixing zone above a continuous molding form. The wider or flanged portion of the mold is positioned away from the mixing zone.

A foraminous belt is positioned on the side of the mold opposite the mixing zone. Thus, the mold is left open toward the mixing zone but covered by the foraminous belt on the flange side.

A vacuum means is provided on the side of the foraminous belt opposite the mold. The vacuum means pulls the entraining air through the foraminous belt. The fibers entrained in the air condense on the belt within the mold. Additional fibers condense on the previously trapped fibers until the mold is filled.

The mold and belt travel out of communication with the mixing zone. Once clear of the mixing zone the mold diverges from the belt leaving the flanged product on the belt for further processing, for example, as a sanitary napkin.

BRIEF DESCRIPTION OF THE DRAWINGS

The invention will now be described with reference to the accompanying drawings wherein:

FIG. 4 is a partial circumferential cross-section of the mold wheel of FIG. 3;

FIG. 5 depicts a second embodiment of the apparatus having a mold belt; and

FIG. 6 is a partial cross-section through one of the molds of the belt in FIG. 5.

DESCRIPTION OF THE PREFERRED EMBODIMENT

Figure 1:
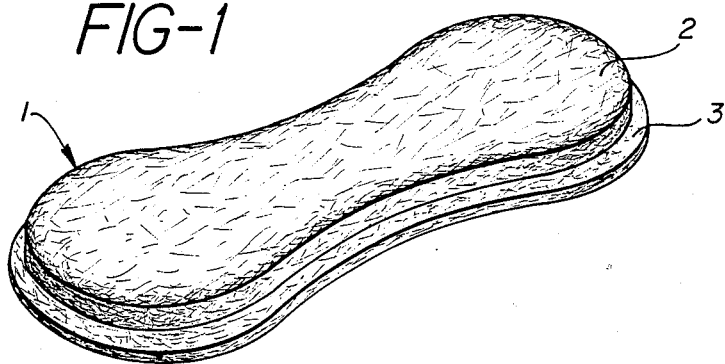
FIG. 1 is a perspective view of a flanged product made by the apparatus of the invention.

Referring now to FIG. 1, a representative product of the present invention is shown. A core 1 for a sanitary napkin is made having a molded figure-eight shape. The core 1 has a main body 2 and a planar flange 3. The body is made of a mixture of fibers which are typically pulp alone or pulp with the addition of textile fibers (i.e. more than 0.25 inches in length). However, by using an apparatus such as that shown in U.S. Pat. No. 3,740,797 to Farrington, the disclosure of which is incorporated herein by reference, to provide a layered structure, the device of the present apparatus permits formation of a product having longer fibers and composite fiber structures. For example, a fusible layer may be created at the flange level with the body 2 being absorbent. Thus, the flange layer may be fused to a backing sheet in a future operation.

Figure 2:
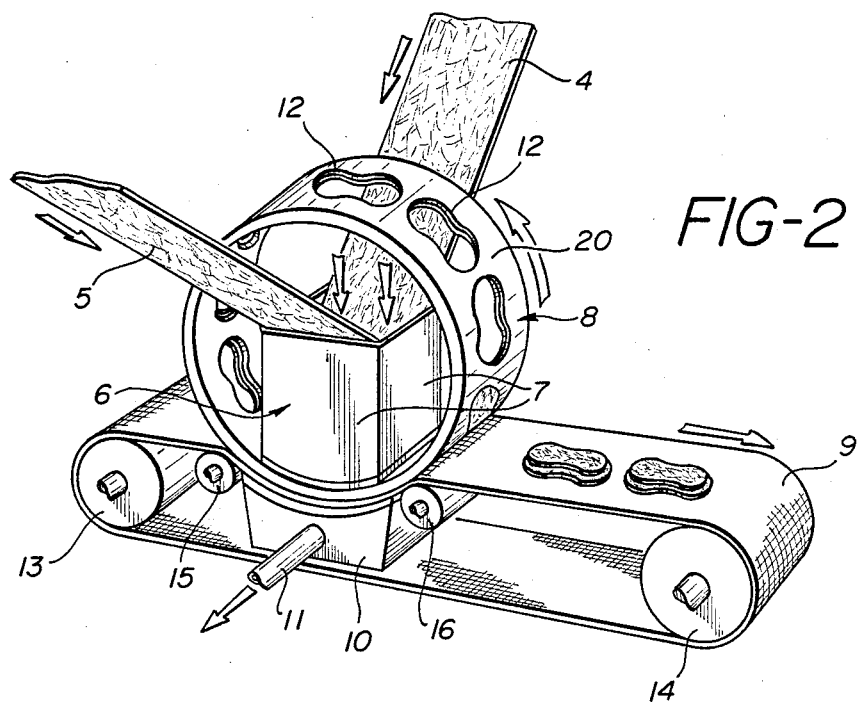
FIG. 2 is a perspective view of a first embodiment of the invention having schematic fiber fields.

To form such a structure, the apparatus of FIG. 2 is used. Two supplies 4,5 of different fibers are introduced into the mixing chamber 6. These fiber supplies are shown schematically as any known air entraining fiber supply methods may be used. Furthermore, more than two supplies may be used in order to provide a multilayered and/or multiblended product.

The fiber supplies may be of any known sort of air entrained fiber supply. For example, pulp stock may be fed to the surface of a rotating toothed lickerin to open and individualize the pulp fibers. These fibers may then be ejected from the lickerin surface into an air stream passing through the mixing chamber 6. A similar supply of textile fibers may be supplied to the surface of a second rotating toothed lickerin, which may be rotating at a different speed. This second lickerin would open and individualize the textile fibers which would then be ejected into the mixing chamber. Fiber supply from two supplies as used herein is known as shown for example by the above mentioned Pat. No. 3,740,797.

The mixing chamber 6 is defined by sealing walls 7 which direct the supplies downward. At the base of the mixing chamber 6 is a continuous mold wheel 8. Opposite mold wheel 8 is a foraminous belt 9 which may be a screen of known type. Belt 9 provides a condensing surface for the entrained fibers.

Opposite the belt 9 is a vacuum box 10 with a duct 11 communicating with a vacuum source (not shown). The vacuum source provides a vacuum to the vacuum box 10 through duct 11. The vacuum pulls the air which entrains the fibers through belt 9. Thus, the entrained fibers are condensed onto belt 9.

Figure 3:
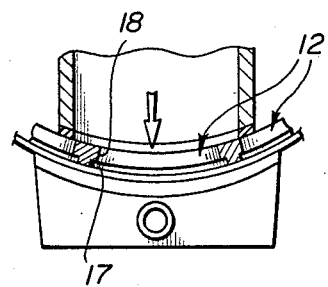
FIG. 3 is a partial cross-section of the embodiment of FIG. 2.

The interrelation between chamber 6, wheel 8, belt 9 and vacuum box 10 are more clearly shown in FIG. 3. Belt 9 and wheel 8 move in the same direction at matching speeds. Thus, as the mold 12 of wheel 8 passes between the mixing chamber 6 and the vacuum box 10, its condensing surface is provided by the portion of belt 9 moving therewith. The fibers fill the mold 12 as it passes beneath the mixing chamber. The mold 12 then passes out from between mixing chamber 6 and vacuum box 10.

After the mold 12 passes out of mixing chamber 6, the belt 9 peels away from wheel 8. The vacuum box 10 may be extended to the divergence or a soft air stream may be blown from within the wheel to assure that the now formed core 1 stays on belt 9. Because the flanges of core 1 were formed at the side of the mold facing belt 9, the flanges move easily out of the mold without interference of the narrower mold portion.

The belt 9 passes over rolls 13,14 at either end of its path. Small contacting rolls 15,16 hold the belt against wheel 8. By adjusting the separation of rolls 13,14 the tension of the belt against the wheel 8 is adjusted.

The mold 12 has a lip portion 17 which forms the flange and a body portion 18 which forms the body. A layered effect may be created by dividing the mixing zone vertically and ducting different fibers through the divisions thus formed. For example, by introducing fusible fibers into the mixing zone at a point near where the mold enters the mixing zone, the fusible fibers will form a lowermost layer. Then, as the mold passes through the remainder of the mixing zones, the remaining fibers are deposited onto the fusible flibers layered without division.

An alternate embodiment is shown in FIGS. 5 and 6. In this embodiment, the molds 111 are provided by a flexible mold strip 108. The strip 108 is directed around rolls 119. The strip 108 is synchronized to belt 109. The strip 108 eliminates the need for rolls 15,16 and the curved portion of belt 9 which is in contact with the face 20 of wheel 8. In this way a planar product may be produced without any stresses such as are formed in the product by forming it in a curved condition and then flattening out the product.

The flexible mold strip 108 forms compound molds similar to those of the wheel 8. The molds are shown in cross-section in FIG. 6. The mold defines a lower flange forming portion 121 which is a larger opening than body forming portion 122. Thus when fibers are deposited within the mold, the flange forming portion 121 will fill first followed by the body forming portion 122. Once the filled mold exits the mixing chamber 6, the mold strip 108 is separated from belt 9 leaving the flanged product. Thus a product is formed having a larger lower portion than the upper body portion and the product is on the belt 9 for transport for further processing without the need to manipulate the product or transfer the product from belt-to-belt. This permits the product to remain in tact by eliminating excessive product stress caused by movement and repositioning.

Many modifications may be made to the apparatus within the scope of the invention. For example, the mold strip 108 may be made of a series of articulable rigid links forming an endless chain which follows a path different from that of strip 108. Furthermore, said mold strip 108 may be made of a laminate of two strips; one defining the flange portion of the mold a a second aligned with the first strip in face-to-face contact therewith to define the body forming portion of the mold. Such a laminate or composite strip may have a sheet of stainless steel interposed between adjacent layers. Such a sheet would support the lateral edges of the mold strip while remaining flexible about an axis transverse to the machine direction.

We claim:

1. In an apparatus for forming a complexly shaped product, the apparatus having at least one fiber supply means to supply opened fibers to an air stream which air stream entrains and transports said fibers to a condensing surface, the improvement comprising:
   (a) a moving foraminous surface forming said condensing surface positioned to pass through said air stream substantially transversely thereto;
   (b) a continuous molding loop defining at least one mold, for receiving entrained fibers from said air stream which are condensed on said foraminous surface within said mold to form a product having a shape defined in part by said mold and said foraminous surface, said mold comprising:
      (i) a first mold portion adjacent said foraminous surface defining an opening of predetermined shape and dimensions; and
      (ii) a second mold portion separated from said foraminous surface by at least said first mold portion and defining an opening of predetermined shape and dimensions which blocks a part of the opening defined by said first mold portion; and
   (c) means for moving said molding loop along a path which passes in part adjacent to and in the same direction of movement as said foraminous surface and in part away from said foraminous surface leaving products formed in said mold deposited on said foraminous surface.

2. The improvement according to claim 1 wherein:
   (a) said moving foraminous surface is comprised of an endless screen passing through said air stream.

3. The improvement according to claim 2 wherein:
   (a) said continuous molding loop is at least one endless flexible belt which travels in face-to-face contact with said screen as said screen passes through said air stream.

4. The improvement according to claim 3 wherein:
   (a) said flexible belt defines at least one complex opening forming said mold.

5. The improvement according to claim 4 wherein:
   (a) said flexible belt is a composite of two flexible belt portions in face-to-face contact; and
   (b) each of said belt portions defines a portion of said mold.

6. The improvement according to claim 3 wherein:
   (a) said flexible belt is comprised of a series of substantially rigid flexible interconnected links forming an endless chain.

7. The improvement according to claim 6 wherein:
   (a) said flexible belt defines at least one complex opening forming said mold.

8. The improvement according to claim 6 wherein:
   (a) said flexible belt is a composite of two flexible belt portions in face-to-face contact, each belt portion being made up of a series of substantially rigid, flexibly interconnected links; and
   (b) each of said belt portions defines a portion of said mold.

9. The improvement according to claim 2 wherein:
   (a) said continuous molding loop is cylindrical and rotates about its longitudinal axis; and
   (b) said screen travels along an outer surface of said cylinder in synchronized face-to-face relation as said screen passes through said gas stream.

10. The improvement according to claim 9 wherein:
   (a) said gas stream is induced by a vacuum source positioned adjacent said screen on a side opposite said cylinder at a point where said cylinder and screen are in face-to-face contact and said vacuum source induces said gas stream to flow through said openings defined in said first and second mold portions.

* * * * *